United States Patent [19]

Clements et al.

[11] Patent Number: 4,905,819

[45] Date of Patent: Mar. 6, 1990

[54] SYSTEM FOR STORAGE AND CARING FOR CONTACT LENSES

[75] Inventors: Don A. Clements, Arlington; Michael J. Kent; William A. Fronk, both of Fort Worth, all of Tex.

[73] Assignee: Alcon Laboratories, Inc., Fort Worth, Tex.

[21] Appl. No.: 235,589

[22] Filed: Aug. 24, 1988

[51] Int. Cl.⁴ .............................................. A45C 11/04
[52] U.S. Cl. .................................... 206/5.1; 134/137; 222/207
[58] Field of Search .................. 206/5.1; 134/24, 34, 134/137; 222/207, 211

[56] References Cited

U.S. PATENT DOCUMENTS

| | | | |
|---|---|---|---|
| 2,940,589 | 6/1960 | Silverman | 206/5.1 |
| 3,054,412 | 9/1962 | Nickell | 134/137 |
| 3,113,579 | 12/1963 | Willis | 134/145 |
| 3,124,240 | 3/1964 | Croan | 206/5.1 |
| 3,326,358 | 6/1967 | Singleton | 206/5 |
| 3,460,552 | 8/1969 | Sturgeon | 134/135 |
| 3,473,886 | 10/1969 | Leeds | 206/5.1 |
| 3,623,492 | 11/1971 | Frantz | 134/143 |
| 3,705,668 | 12/1977 | Schwartzman | 222/207 |
| 3,856,571 | 12/1974 | Sherman | 206/5.1 |
| 4,036,357 | 7/1977 | Czelen | 206/5.1 |
| 4,077,547 | 3/1978 | Donoghue | 222/207 |
| 4,089,552 | 5/1978 | Hermanson | 206/5.1 |
| 4,106,673 | 8/1978 | Donoghue | 222/207 |
| 4,429,786 | 2/1984 | Hucal | 206/5.1 |
| 4,444,307 | 4/1984 | Jermyn | 206/5.1 |
| 4,776,360 | 10/1988 | Ching Shih | 206/5.1 |

Primary Examiner—David T. Fidei
Attorney, Agent, or Firm—James A. Arno; Gregg C. Brown; Sally Stewart

[57] ABSTRACT

A means, method, and system for storing and caring for contact lenses, including cleaning, rinsing, storing, disinfecting, lubricating, etc., including a self-contained contact lens holder to support and contain one or more contact lenses. A fluid conduit is associated with the contact lens holder to provide a pathway for fluid to the chamber or chambers holding each contact lens. A fluid container holding a fluid used in contact lens care can be put in fluid communication with the fluid conduit and is operable to selectively introduce fluid into the fluid conduit and fill the contact lens holder with the fluid. The contact lens holder, fluid contact, and fluid container may all be incorporated in a unitary body, or fluid container and/or the fluid conduit can be selectively attachable to the contact lens holder so that different fluid containers can be interchangeable to the contact lens holder. In another aspect of the invention, the structure can be adjustably oriented with respect to the contact lens holder to allow rinsing of the contact lens holder after use, while retaining the contact lens within the contact lens holder. Another aspect of the invention allows optional attachments for the carrying of other contact lens care products within or associated with the contact lens holder.

13 Claims, 6 Drawing Sheets

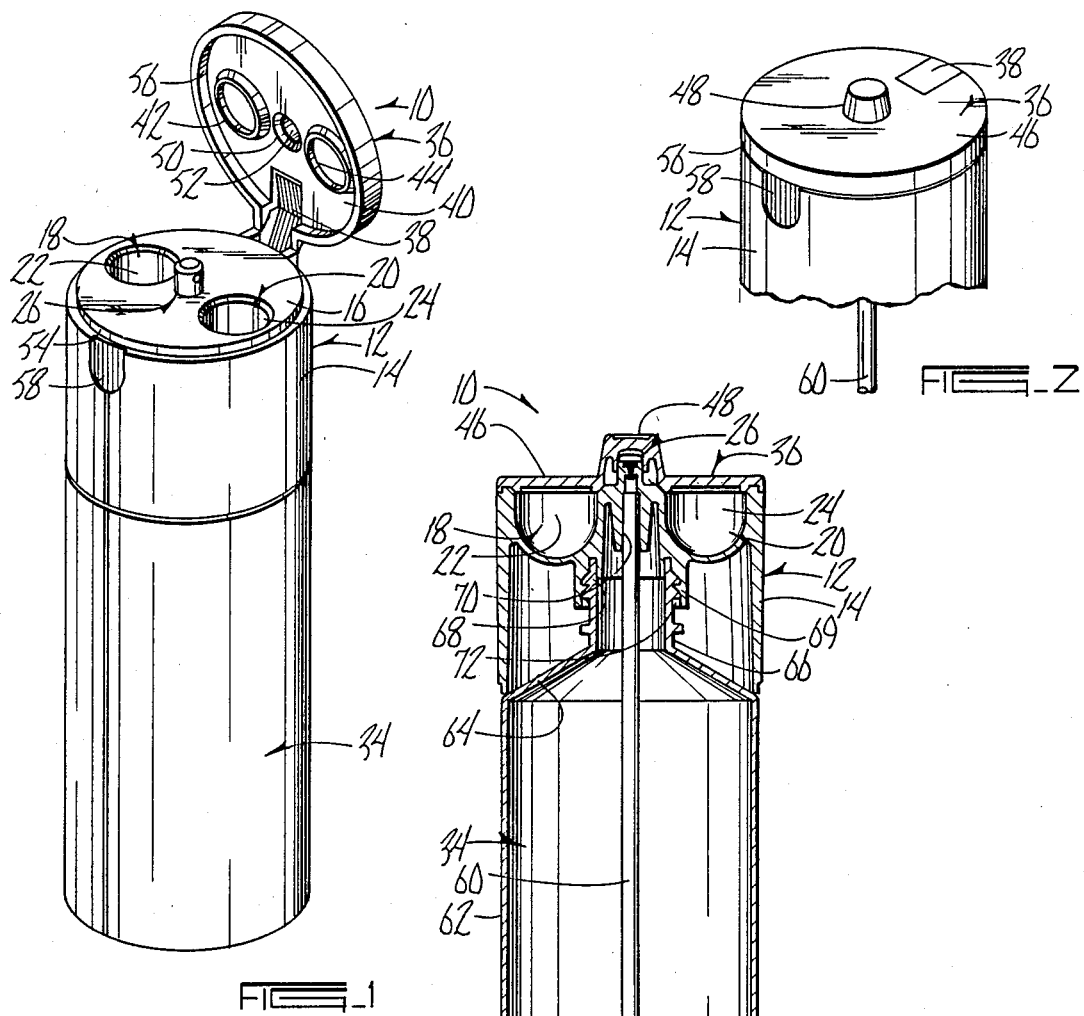
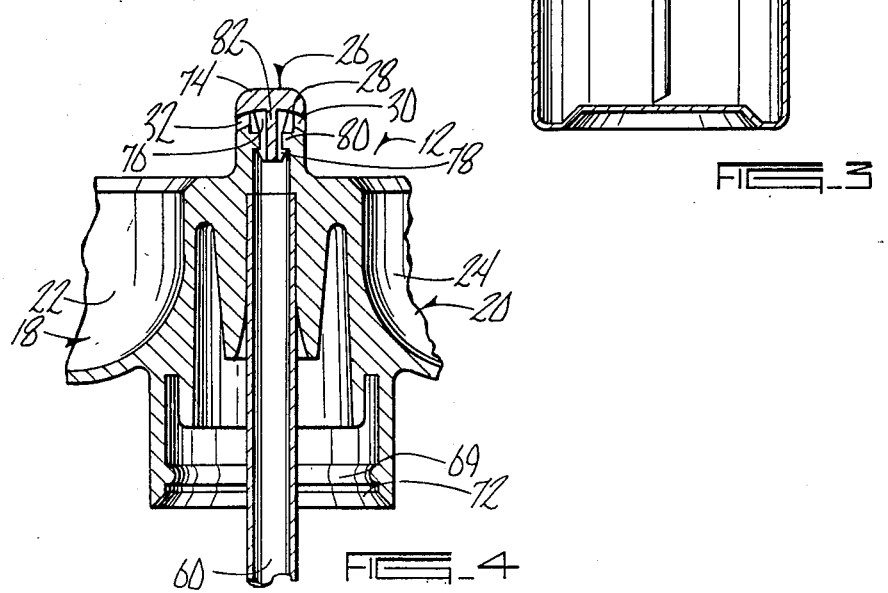

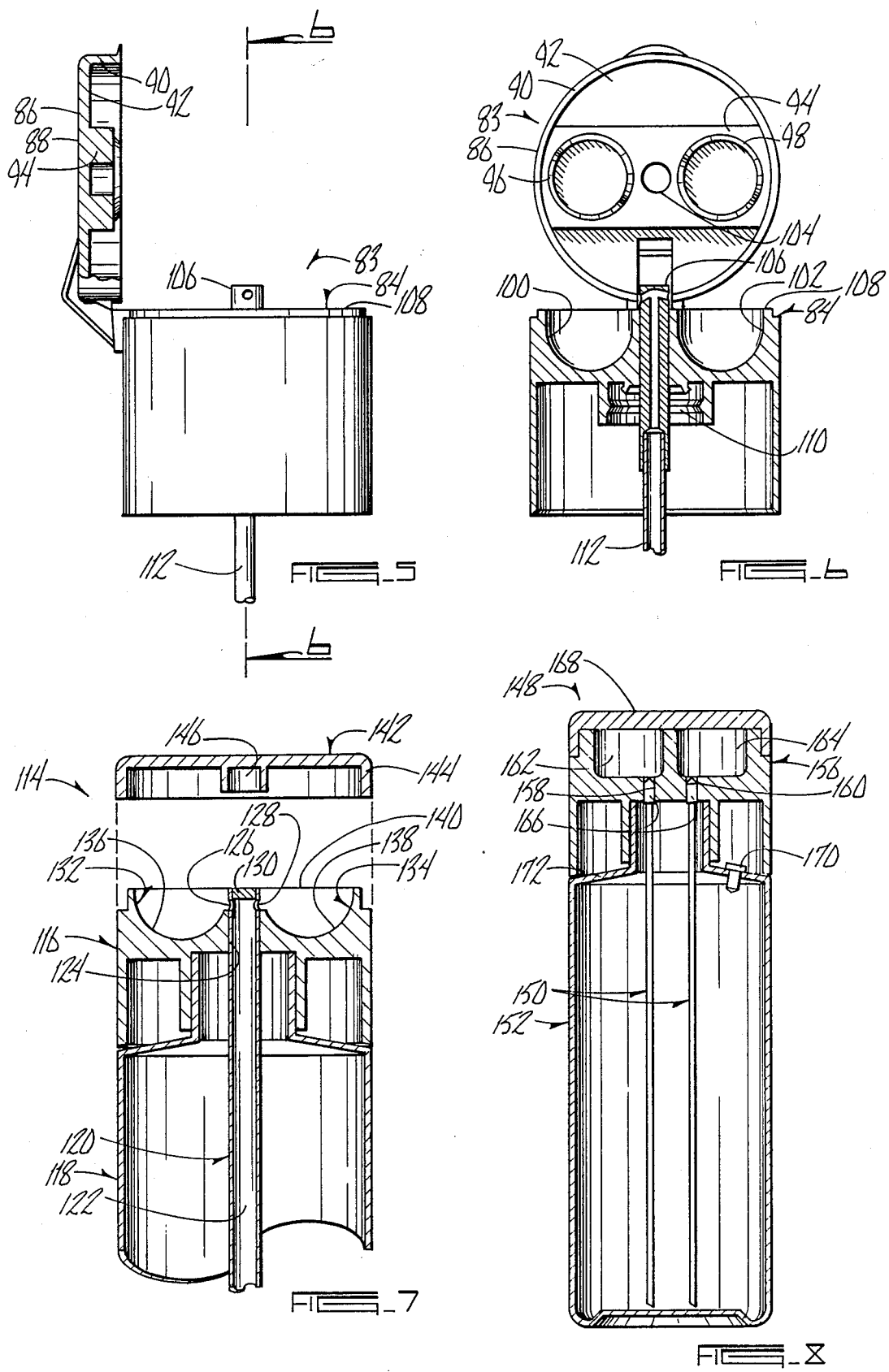

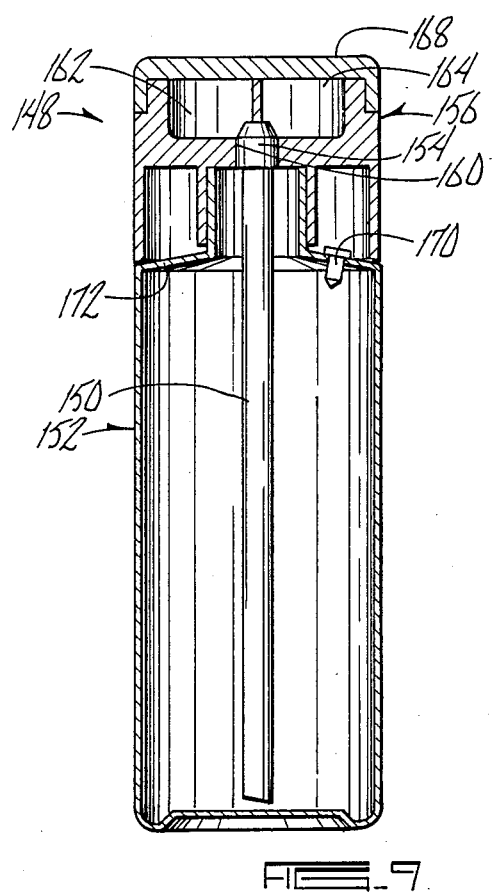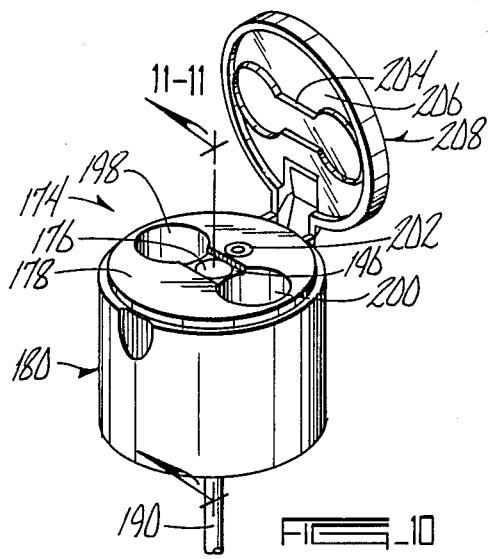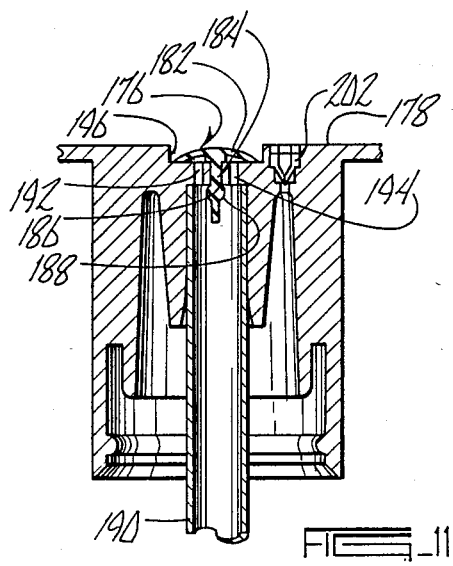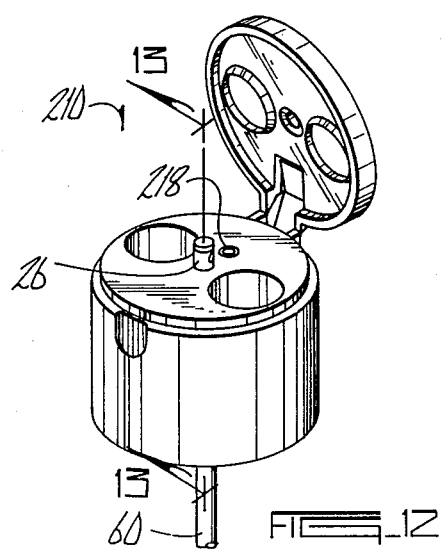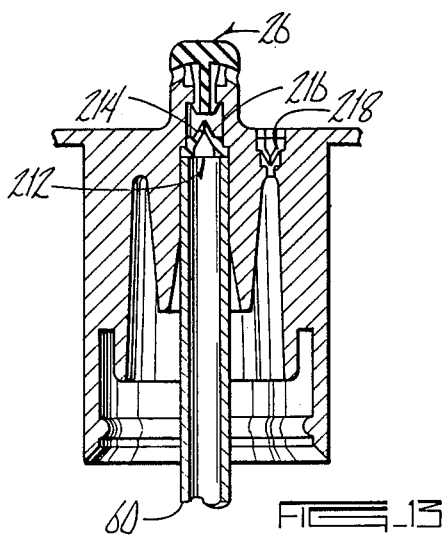

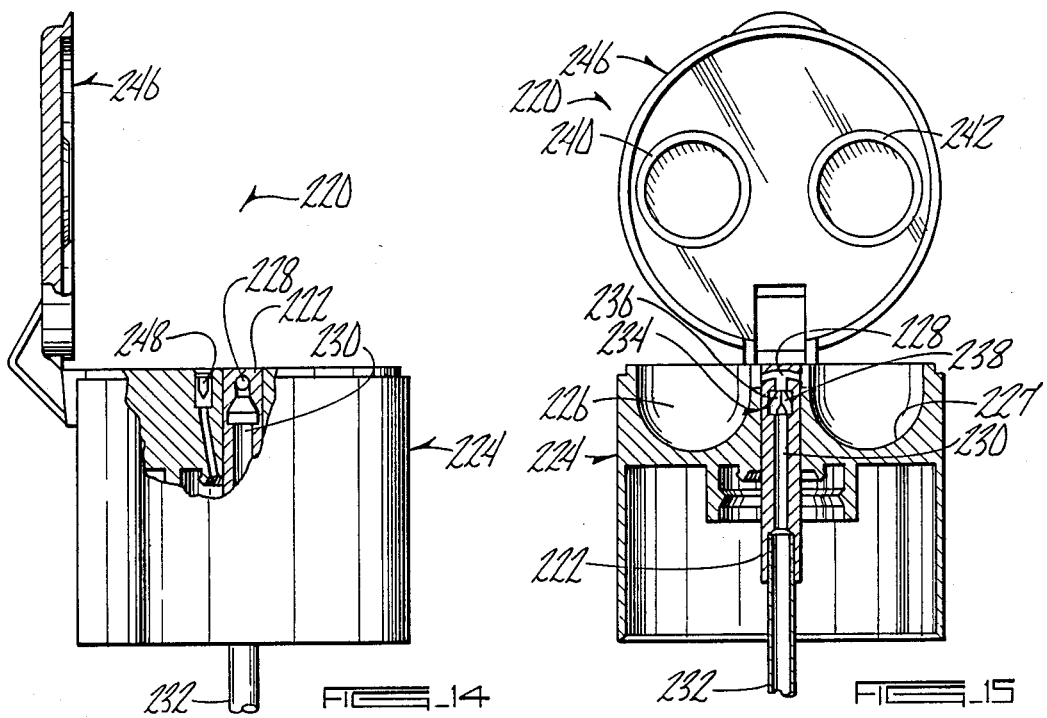
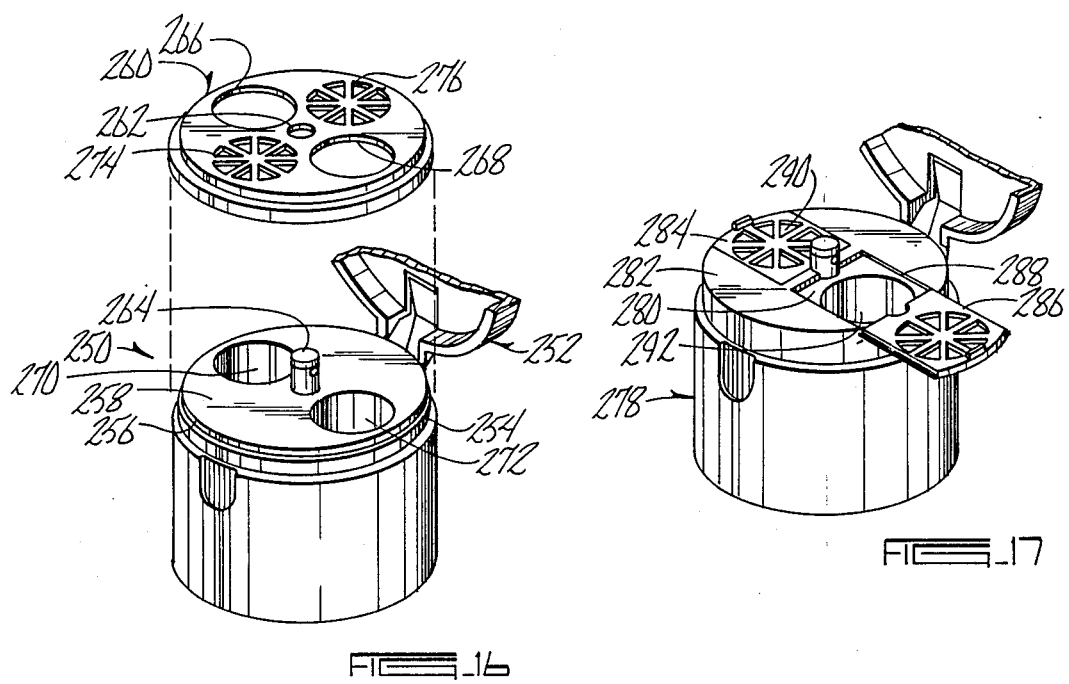

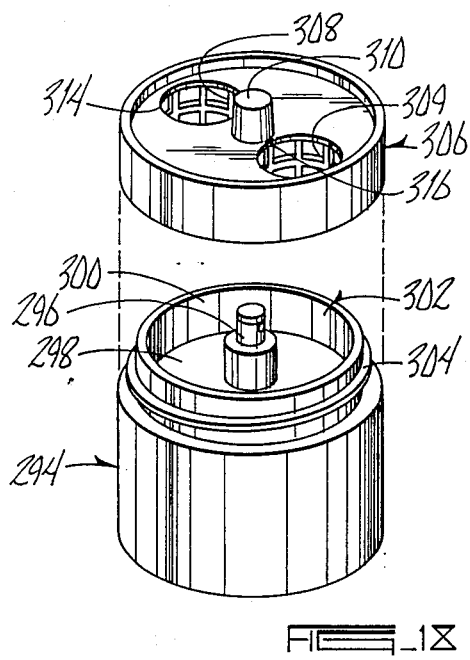
FIG_18
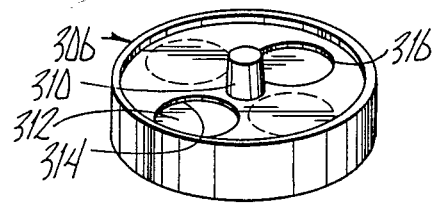
FIG_17
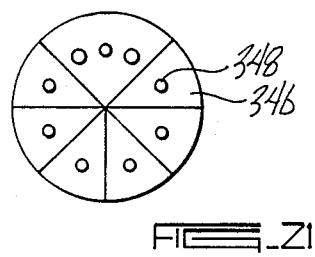
FIG_21
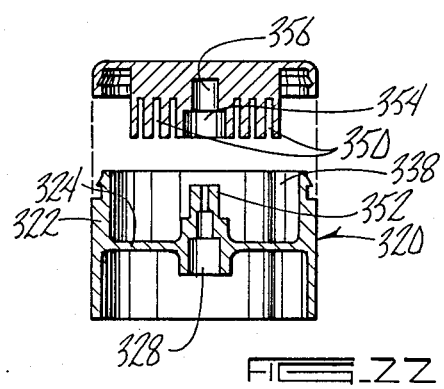
FIG_22
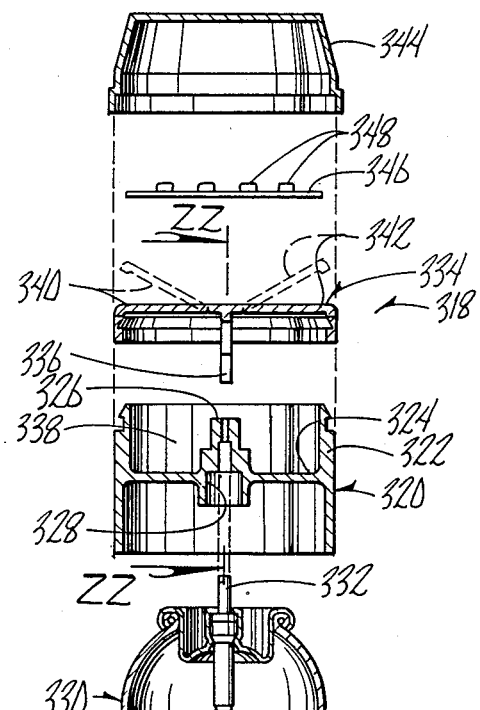
FIG_20

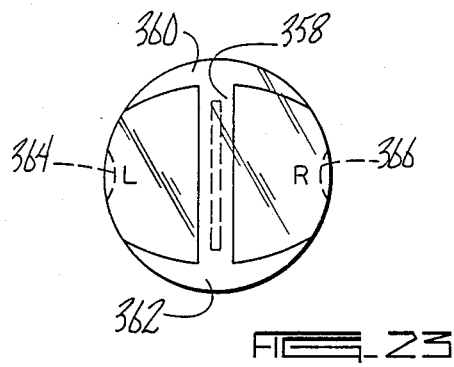
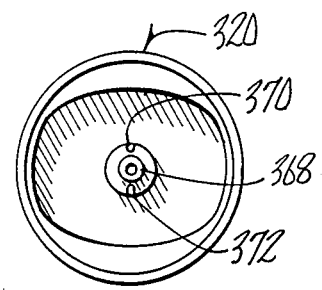
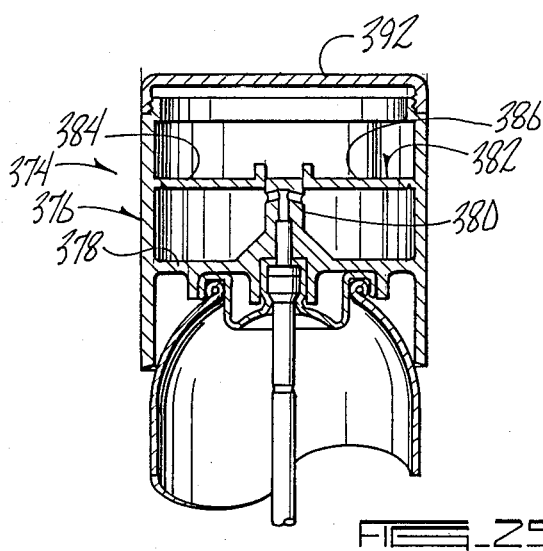
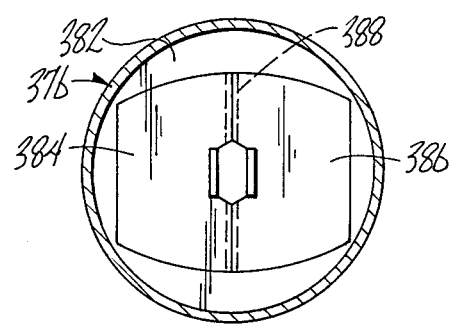
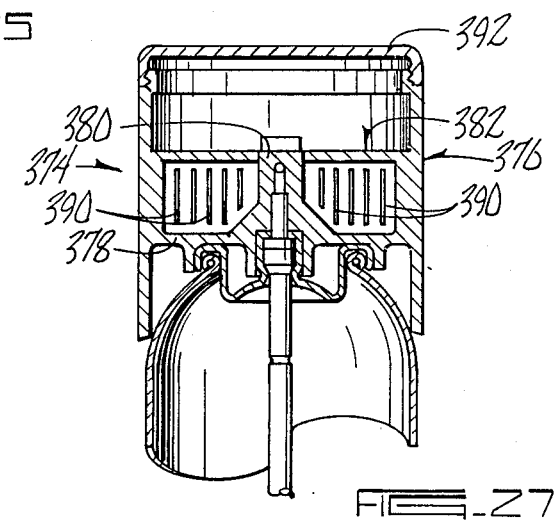

SYSTEM FOR STORAGE AND CARING FOR CONTACT LENSES

BACKGROUND OF THE INVENTION

1. Field of the Invention.

The present invention relates to care for contact lenses, and in particular, to cleaning, rinsing, storing, disinfecting, lubricating, and the like with respect to contact lenses

2. Problems in the art.

Contact lenses have proven to be a desirable alternative to eye glasses. However, they require significant and repetitive maintenance and care. Because of the sensitive and fragile nature of the human eye, and the close association of contact lenses to the eye, to maintain comfort and useability, periodic treatment of contact lenses is necessary.

Depending on the nature of the contact lens, the recurring periods for care and maintenance differ, but the functions are similar. For example, all contact lenses must be kept clean from foreign matter to maintain clarity and reduce abrasion to both the contact lens and the user's eye. Some lenses require periodic disinfecting, and others require periodic lubrication. Furthermore, because of the nature of these type of substances, the contact lenses must be thoroughly rinsed and cleaned before being reused.

Some contact lenses require periodic soaking to maintain a level of wetness to allow optimal comfort for a user. Furthermore, when contact lenses are not being used, their fragile and transparent nature require a secure and generally aseptic place for storage. Many times this is in some sort of a soaking, cleaning, or storage fluid.

It furthermore should be understood that because contact lenses, like eye glasses, many times differ in their optical properties from the left to the right eye, it is desirous that any contact lens holder be configured so that the user can easily discern and identify the storage place for the left contact lens in contrast to the right contact lens, especially when the user's vision is generally impaired when contact lenses are out of the user's eyes.

Conventionally, contact lens storage holders are small two-chambered devices, with either screw-on caps, or snap-down caps. To introduce the fluid for the care of the contact lenses, a specified fluid container, such as a squeeze bottle or the like, holding the desired fluid is obtained, and then the contact lens holder is opened up, and the fluid directed into each chamber holding a lens. The caps or lids are then re-covered over the chamber. Any removal of the fluid requires care that the contact lenses not be lost, requires rinsing, and then any refilling with the fluid, or any other fluid, requires the same steps.

Some attempts have been made to combine a contact lens holder with containers carrying some of the needed fluids for care of contact lenses. These attempts have tried to avoid having a contact user carry a separate contact lens holder, with separate contact lens fluid containers. Some of these attempts have simply configured a holder to either be permanently attached, or removeably attached to a fluid container. However, it still requires that a contact lens holder or holders be opened up, and the fluid container be opened and oriented to fill the contact lens holder with fluid. This is only a slight improvement over conventional contact lens holders, and in fact, may be more cumbersome. The problem still exists with respect to accuracy in filling the lens holder.

Other attempts have configured a container which is filled with fluid, then the contact lenses are put in some sort of a cage or fluid permeable device, and then inserted into the container. These devices also require multiple steps and handling of a separate fluid bottle to fill the container.

There has also been an attempt whereby a device has an upper chamber and a lower fluid container. The lower fluid containerer is filled with the desired fluid. The contact lenses are put in some sort of a cage or a fluid permeable frame which is inserted into an upper chamber in the device. Fluid from the lower container is then conveyed to the upper container, having the frame holding the contact lens, by squeezing or otherwise causing the fluid to be appropriately transported. This again requires special handling of the contact lenses, and numerous steps to achieve its purpose. Such an arrangement is also not generally suitable as a contact lens holder per se.

Therefore, there is a real need to simplify, economize, and make more efficient the means and method for caring for contact lenses. Presently available devices and methods involve fairly complicated structure, require significant handling, and generally utilize separate containers for the lenses and the fluids.

Because contamination is one of the biggest problems with contact lenses, every handling of the lenses, and any part of their containers, including the fluid containers, increases the risk of contamination.

Separate filling of a contact lens holder from an independent fluid container creates accuracy problems. Sufficient fluid is needed in the chamber holding the contact lens to accomplish the function of the fluid, whereas excess creates waste. Also, it is many times cumbersome to handle a separate fluid container, again, especially when the user's contact lenses are out of their eyes.

It is therefore a primary object of the present invention to provide a means, method and system for storing and caring for contact lenses which overcomes or solves the problems and deficiencies in the art.

A further object of the present invention is to provide a means, method and system as above described which allows storage and caring for contact lenses in a unitary apparatus.

Another object of the present invention is to provide a means, method and system as above described, which allows secure, sealable, and easy placement and storage of contact lenses.

A further object of the present invention is to provide a means, method and system as above described, which provides for easy, economical, and efficient storage of contact lens care fluid and communication of that fluid with the contact lens holder.

Another object of the present invention is to provide a means, method and system as above described which eliminates multiple steps and handlinq, with regard to storage of the contact lenses, and measuring and pouring of contact lens care fluid.

A further object of the present invention is to provide a means, method and system as above described, which is economical to manufacture, and non-complex in structure, durable, and economical and easy to use.

A further object of the present invention is to provide a means, method and system as above described which enhances accuracy and efficiency of use of lens care fluids.

Another object of the present invention is to provide a means, method and system as above described which promotes an aseptic and non-contamination environment for the storage, handling and care for contact lenses.

These and other objects, features, and advantages of the invention will be made clearer with reference to the accompanying specification and claims.

SUMMARY OF THE INVENTION

The present invention includes a means, method and system for storing and caring for contact lenses, including, but not limited to, cleaning, rinsing, storing, disinfecting, and lubricating contact lenses while in a holder. The invention allows easy and accurate placement and storage of contact lenses in a holder, while at the same time provides easy and accurate filling of the holder with a desired fluid used in the care of contact lenses.

The first aspect of the invention involves a contact lens holder having a chamber for supporting and containing each contact lens. A cap or other cover can be adjustably positioned to enclose each chamber. A fluid conduit means is associated with the holder and provides a pathway for fluid to each chamber. The holder and conduit then include apparatus to communicate with a fluid container holding a desired lens care fluid. The container can either be unitary with the holder, or can be removable or interchangeable with other fluid containers. The contact lenses can thus be securely stored, or fluid from the fluid container can be accurately dispensed into the holder.

In another aspect of the invention, the fluid conduit can include a distributor means for directing fluid to multiple chambers in the contact lens holder. The fluid conduit can also either consist of a direct pathway between the fluid container and the holder, or can contain one way valves allowing fluid to pass from the container to the holder, but disallowing the passage of fluid from the holder back to the container.

A further aspect of the invention involves structure which can be adjustably positioned with respect to the chambers holding the contact lenses in the contact lens holder providing screens, strainers, or cages to retain the lenses in the chambers, yet allow fluid or pressurized fluid to pass therethrough for rinsing or other purposes. The apparatus can be adjusted between presenting a screen, grate, or cage with respect to the contact lenses, to simply allowing an opening to the chambers for easy access to the contact lenses.

A further aspect of the invention involves the manner in which fluid from the fluid container is conducted to the holder. In one embodiment, the fluid container consists of a squeezable bottle wherein squeezing causes the movement of fluid through an outlet from the bottle through the fluid conduit to the holder. A second embodiment utilizes an aerosol container whereby movement of the lens holder with respect to the fluid container causes expulsion of fluid from the aerosol fluid container into the holder.

A still further aspect of the invention involves an optional attachment to the holder for storing other contact lens care items such as tablet form chemicals, which can be introduced into the contact lens holder with fluid for contact lens care purposes. The invention, in its many aspects, therefore presents a means, method and system for storing and caring for contact lenses which provides ease of use, accuracy, security, and efficiency for contact lens users. It also provides an economical and efficient system to manufacture, package, and market.

BRIEF DESCRIPTION OF THE DRAWINGS

FIG. 1 is a perspective view of one embodiment of the invention, showing the contact lens holder lid in an open position.

FIG. 2 is a partial perspective view with a cut-away portion of the embodiment of FIG. 1, showing the holder lid in a closed position.

FIG. 3 is an elevational cross-sectional view of the embodiment of FIG. 1 with the holder lid in a closed position.

FIG. 4 is an enlarged elevational sectional view of a portion of FIG. 3.

FIG. 5 is an elevational view of the contact lens holder portion of an alternative embodiment of the invention, with the holder cap shown in cross-section and in an open position.

FIG. 6 is a sectional view taken along lines 6—6 of FIG. 5.

FIG. 7 is an elevational cross-sectional view of a still further embodiment of the invention, showing a removable cap for the contact lens holder in a removed position.

FIG. 8 is an elevational cross-sectional view of another embodiment of the invention, including a one way valve between the fluid holding container and the contact lens holder.

FIG. 9 is a side elevational cross-sectional view of the embodiment of FIG. 8.

FIG. 10 is a perspective view of a contact lens holder for an additional embodiment of the invention showing the lid for the holder in an open position.

FIG. 11 is a side elevational cross-sectional view taken along lines 11—11 of FIG. 10.

FIG. 12 is a perspective view of the contact lens holder of a further embodiment of the present invention with the holder lid in an open position.

FIG. 13 is a side elevational cross-sectional elevational view shown along lines 13—13 of FIG. 12.

FIG. 14 is a side elevational view of another embodiment of the contact lens holder of the present invention, with the holder lid shown in cross-section and in an upright position, and with a cut-away portion showing a return air valve.

FIG. 15 is a front elevational cross-sectional view taken along lines 15—15 of FIG. 14.

FIG. 16 is a perspective view of another embodiment of the invention showing a contact lens holder with a lid partially shown in an open position, and a removable rotatable adjustment member which can be positioned over the contact lens holding chambers.

FIG. 17 is a perspective view of another embodiment of the contact lens holder of the present invention similar to that of FIG. 16, showing adjustable strainers which can be positioned over the contact lens holding chambers.

FIG. 18 is a still further embodiment of the present invention showing a contact lens holder, with a removable head portion which includes cages for holding the contact lens.

FIG. 19 is a perspective view of the head portion of the embodiment of FIG. 18 showing that a portion can be adjusted to close off the openings into the cages for holding the contact lenses.

FIG. 20 is a front elevational cross-sectional exploded view of a further embodiment of the present invention including an aerosol fluid container, a contact lens holder having a cap with hingeable lids to each contact lens chamber, and an overcap for releaseably holding contact lens care chemical tablets to the contact lens holder.

FIG. 21 is a top plan view of a tablet sheet for the embodiment of FIG. 20.

FIG. 22 is a side elevational cross-sectional view of the cap and the distributor head for the lens holder of the embodiment of FIG. 20.

FIG. 23 is a top plan view of the cap for the lens holder of the embodiment of FIG. 20.

FIG. 24 is a top plan view of the lens holder of the embodiment of FIG. 20.

FIG. 25 is a partial elevational cross-sectional view of a further embodiment of the invention similar to that of the embodiment of FIG. 20.

FIG. 26 is a top plan view of the cap for the embodiment of FIG. 25, having hinged lids for access to the chambers holding contact lenses.

FIG. 27 is a partial side elevational cross-sectional view of the interior of the lens holder for the embodiment of FIG. 25.

DETAILED DESCRIPTION OF THE PREFERRED EMBODIMENTS

With reference to the drawings, a detailed description of the preferred embodiments of the invention will follow. Reference numerals will be utilized to identify certain features and parts of the embodiments. Like reference numerals will be used to identify like parts in the drawings. The drawings and these detailed descriptions are intended to give the reader an understanding of some of the different forms the invention might take, and some of the different features the invention might include. These examples are not intended to and do not limit the scope of the invention.

With particular reference to FIG. 1, first embodiment 10 of the invention is shown in perspective. A contact lens holder 12 includes an annular side wall 14 and a top wall 16. Recessed chambers 18 and 20 are defined by cupped walls 22 and 24 extending downwardly from top wall 16 and interiorly of annular side wall 14. Chambers 18 and 20 receive left and right contact lenses, support them, and also can receive fluids for storage, cleaning, rinsing, disinfecting, lubricating, and other functions with respect to contact lenses.

A distributor head 26 of fluid conduit 28 (see also FIGS. 2-4), extends upwardly from or through top wall 16 and includes orifices 30 and 32 on opposite lateral sides which are directed towards chambers 18 and 20, respectively. The fluid through fluid conduit 28 and distributor head 26 thus is directed by orifices 30 and 32 into chambers 18 and 20 when desired.

Lens holder 12 is positioned on top of a fluid container 34, which holds fluid for lens care. Fluid conduit 28 is in fluid communication with the interior of fluid container 34. It is to be understood that fluid container 34 could be integrally formed with lens holder 12, but is preferred that fluid container 34 be removably securable to lens holder 12 and fluid conduit 28 so that replacement of fluid container 34 or interchangeability of containers holding different lens care fluids can be easily accomplished.

A lid or cap 36 is hingeably connected to lens holder 12 by hinge 38. Bottom side 40 of cap 36 contains two downwardly extending rings 42 and 44 which are positioned so as to mateably fit within the recessed chambers 18 and 20 in lens holder 12. Ideally, rings 42 and 44 would fixedly fit therein and seal any fluid inlet or outlet to chambers 18 and 20.

Top side 46 of cap 36 includes an extended portion 48 which covers aperture 50 in the center of cap 36. A cavity 52 extends up into extended portion 48 from aperture 50, to allow distributor head 26 to be inserted therein when cap 36 is moved from its open position shown in FIG. 1, to a closed position (shown in FIG. 2). It is to be understood that aperture 50 and cavity 52 could be configured so as to sealingly fit over distributor head 26 to deter any fluid passage from distributor head 26. Lens holder 12 can also have a raised edge 54 to cooperate with annular flange 56 of cap 36 to cause a secure fit between cap 36 and lens holder 12 when in a closed position. A notch 58 in the side wall 14 of lens holder 12 would permit access to annular flange 56 of cap 36 to raise it from the closed position shown in FIG. 2. This configuration would allow embodiment 10 to have a smooth annular side wall from cap 36 down through lens holder 12 and fluid container 34.

FIG. 2 not only shows cap 36 in a closed position, but also shows tube 60 of fluid conduit 28. Tube 60 would form a fluid passageway between fluid container 34 and distributor head 26 and could either be permanently secured to lens holder 12, or be removable. If tube 60 and fluid container 34 were removable from lens holder 12, lens holder 12 with cap 36 could function independently as a contact lens holding case.

FIG. 3 shows in elevational cross-section, the general configuration of the interior of lens holder 12, including cap. 36, fluid conduit 28, and fluid container 34. Cap 36 is shown in the closed position covering cupped walls 22 and 24 defining chambers 18 and 20 for holding left and right contact lenses. Walls 22 and 24 are cupped to provide easy insertion and removal of the small fragile contact lenses, and also to allow thorough cleaning of chambers 18 and 20, by eliminating any corners. FIG. 3 shows that fluid container 34 has a basically tubular body 62 topped by upwardly angled shoulder 64, and neck 66. The exterior of neck 66 includes threads 68 which mateably engage threaded socket 69 extending downwardly from the outside of cupped walls 20 and 22 of lens holder 12.

Fluid container 34 thus can be threaded into socket 69 until the bottom of annular side wall 14 of lens holder 12 abuts shoulder 64 of fluid container 34. Lens holder 12 and fluid container 34 would then be firmly secured together in a sealing relationship.

Fluid conduit 28 includes tube 60 extending from near the bottom of the interior of fluid container 34 up through neck 66 of fluid container 34, and socket 69 of lens holder 12 into a bore 70 in lens holder 12. Bore 70 has a wider lower end 72 which receives tube 60, but then narrows to frictionally grasp and secure tube 60 therein. Bore 70 also extends to distributor head 26 to allow a complete fluid passage from fluid container 34 to distributor 26.

As can be seen in FIG. 3, when lid 36 is in a closed position, fluid cannot travel from fluid container 34 out of distributor head 26, or into chambers 18 and 20. Furthermore, fluid cannot pass out of chambers 18 and 20.

FIG. 4 shows in enlarged detail that distributor head 26 has an enlarged head 74 and a downward extending portion 76, so that distributor head 26 is generally T-shaped in cross-section. Portion 76 has at its lower end a smaller head 78 which cooperates with interior annular flange 80 of lens holder 12 to allow distributor head 26 to be snapped-in to position. Orifices 30 and 32 exist on opposite sides of divider wall 82 of downwardly extending portion 76. Divider wall 82 serves to direct fluid traveling up tube 60 and bore 70 equally into orifices 30 and 32. It is to be further understood that orifices 30 and 32 are in a raised position above top wall 16 of lens holder 12, but in a somewhat downwardly angled orientation so that fluid under pressure will be directed in a stream or focused spray into recessed chambers 18 and 20. Orifices 30 and 32 are configured so as to form an easily controlled directional stream to each recessed chamber 18 and 20 to enhance accuracy and avoid waste. Furthermore, fluid conduit 28 is configured so that by squeezing the flexible and resilient body 62 of fluid container 34, pressure will cause fluid to travel up tube 60 into distributor head 26 for easy and controllable filling of chambers 18 and 20, and easy and controllable stoppage of filling by releasing pressure on tubular body 62.

FIGS. 5 and 6 depict a lens holder 84 which is slightly different from lens holder 12 of embodiment 10, but operates upon the same principles. Lens holder 84 differs only in that instead of having an extended portion raising from the middle of the cap, to produce a protrusion, cap 86 of lens holder 84 has a flat top surface 88. The annular side wall 90 of cap 86 is taller than annular flange 56 of cap 36 of embodiment 10. Bottom side 92 of cap 86 of lens holder 84 has a solid portion 94 which includes springs 96 and 98 for sealing off cupped chambers 100 and 102 in lens holder 84. Solid portion 94 also includes a straight center bore 104 which would cover and contain distributor head 106.

It can also be seen that distributor head 106 stands from outside and above top wall 108 of lens holder 84, all the way down through threaded socket 110. It then receives tube 112. This arrangement differs slightly from that of embodiment 10 shown specifically in FIGS. 3 and 4, but operates essentially the same. FIG. 7 shows a still further embodiment 114 of the invention, similar to embodiments 10 and 83 previously described. Embodiment 114 utilizes a lens holder 116 and a fluid container 118 which function as described with respect to previous embodiments. However, in embodiment 114, fluid conduit 120 is comprised solely of tube 122 which extends from fluid container 118 through bore 124 in lens holder 116. Tube 122 has small orifices 126 and 128 near its top end, and a plug 130 above orifices 126 and 128 in its top end. Cup chambers 132 and 134 have adjacent inner side walls 136 and 138 which are lowered in the position of orifices 126 and 128 so that cup chambers 132 and 134 can be in direct fluid communication with orifices 126 and 128 and tube 122. Thus, there is no distributor head which extends above top wall 140 of lens holder 116. Orifices 126 and 128 are positioned so that fluid can fill in cup chambers 132 and 134 to a level to cover contact lenses positioned therein, but fluid will not drain out back into the tube 122 unless filled up to orifices 126 and 128.

Cap 142 thus simply fits around annular wall 144 of lens holder 116, and contains a sleeve 146 which surrounds orifices 126 and 128 and tube 122 when positioned upon lens holder 126, this serves to seal off any fluid communication between chambers 132 and 134, and orifice 126 and 128.

FIGS. 8 and 9 depict embodiment 148 which functions similarly to embodiments 10, 83 and 114 except as follows. Tube 150 extends from the bottom of fluid container 152 to a one way valve assembly 154 positioned in lens holder 156 (see particularly FIG. 9). As schematically shown in FIG. 8, one way valve assembly 154 consists of parallel channels 158 and 160 which extend from tube 15 into cupped chambers 162 and 164, respectively. Each channel contains a one way valve 166 such as are known in the art. In the embodiment of FIG. 8, valves 166 are called "duck-bill" valves as they open when fluid under pressure from tube 150 forces against them to allow fluid into chambers 162 and 164, but close when fluid under pressure through tube 150 is relaxed.

Cap 168 removably is securable over cup chambers 162 and 164 to allow access thereto. Fluid container 152 can either be secured to lens holder 156, or be detachable, such as previously described. Tube 150 could either form a part of lens holder 156 or fluid container 152, or could be detachable from either.

In order to enhance operation of the embodiment of FIGS. 8 and 9, an air valve 170 is positioned through an aperture in shoulder 172 of fluid container 152. Air valve 170 functions as is known in the art, similarly to a one-way valve, by sealing off fluid container 152, except after it is squeezed, when valve 170 operates to allow a supply of air into the interior of fluid container 152, but disallowing any fluid to escape therethrough. Thus, squeezing of fluid container 152 operates to build up pressure in container 152 to force fluid up tube 150, but upon release of fluid container 152, air valve 170 allows equalization of pressure in fluid container 152, and allows it to return to its original state.

FIGS. 10-15 show alternative embodiments for a lens holder utilizing a valve in the fluid conduit. In FIGS. 10 and 11, there is shown embodiment 174 wherein a one way valve 176, called an "umbrella valve" is positioned in top wall 178 of lens holder 180. As can be seen most clearly in FIG. 11, umbrella valve 176 is comprised of a head portion 182 attached to a stem portion 184 which slidably is positioned in bore 186 through top wall 178. A biasing member 188 holds umbrella valve 176 in the position shown in FIG. 11. However, when fluid under pressure flows up tube 190, according to the manner previously described with other embodiments, the fluid will pass through parallel bores 192 and 194 which communicate with tube 190 and cause head portion 182 of umbrella valve 176 to move upwardly. The fluid would then flow in duct 196 to both chambers 198 and 200 holding the lenses. Upon release of pressure up through tube 190, biasing member 188 would force umbrella valve 176 back to a covering relation over bores 192 and 194.

FIGS. 10 and 11 also show a one way duck bill valve 202 which functions as an air valve similar to that described with respect to embodiment 148 in FIGS. 8 and 9. FIG. 10 further shows that a flange 204 can be positioned on the bottom side 206 of cap 208 of embodiment 174 and be of such a configuration that it follows the enclosed shape defined by duct 196, and portions of the perimeter of chambers 198 and 200, so that if desired, the fluid can flow between chambers 198 and 200, or one way valve 176 can operate even if cap 208 is in closed position. On the other hand, it can be configured so that when cap 208 is in a closed position, it does not permit one way umbrella valve 176 from opening. This can be designed according to choice.

FIGS. 12 and 13 show embodiment 210 which is essentially the same as embodiment 10 shown in FIGS. 1–4 except that a duck bill one-way valve 212 is positioned on tube 60 and distributor head 26 in bore 70. Again, when fluid under pressure travels up tube 60, opposite sides 214 and 216 open to allow passage of the fluid to distributor head 26. When pressure decreases to less than the closing biasing force of sides 214 and 216, sides 214 and 216 close off any fluid communication through valve 212 in either direction. Additionally, FIG. 13 shows duck bill one way valve 218 utilized as an air vent for embodiment 210.

Embodiment 220 of FIGS. 14 and 15 is depicted to show an alternative embodiment for the invention whereby a distributor head 222 is positioned in lens holder 24 between chambers 226 and 228, similarly to the embodiment depicted by reference numeral 114 in FIG. 7. Distributor head 222 includes a T-shaped passage 228 which communicates with passage 230, which in turn communicates with tube 232. A duck bill one way valve 234 is positioned in passage 230 directly before T-shaped passage 228 in a manner in which halves or sides 236 and 238 open when fluid pressure of a sufficient force is exerted through tube 232 to distribute fluid through T-shaped passage 228 into chambers 226 and 227.

Two ring flanges 240 and 242 on the bottom side of cap 246 could seal off chambers 226 and 227 when cap 246 is in a closed position. One way valve 234 would eliminate the need for any other structure in cap 246 to seal off T-shaped passage 228.

FIG. 14 also shows that a return air valve 248 could be positioned in lens holder 224 and function as previously described in other embodiments.

FIG. 16 shows another aspect of the invention. A lens holder 250, similar in function to embodiment 10 of FIG. 1, or embodiment 210 of FIG. 12, having a hinged cap 252, could also contain threads 254 along raised vertical edge 256 around the perimeter of top wall 258 of lens holder 250. A rotatable cover member 260, having threads (not shown) matable with threads 254, can optionally be threaded onto threads 254 of lens holder 250. As can be seen, cover member 260 has a center aperture 262 through which distributor head 264 would slidably pass. On opposite sides of aperture 262 are apertures 266 and 268 which are generally the same diameter as chambers 270 and 272 in lens holder 250. By threading cover member 260 upon lens holder 250 to where apertures 266 and 268 are aligned with chambers 270 and 272, access to chambers 270 and 272 is the same as if cover member 260 were not in position on lens holder 250. Thus, contact lenses can be inserted and withdrawn and cap 252 can be closed down to secure lenses therein. Also, lens holder 250 could be operated in association with a fluid container to fill chambers 270 and 272 with lens care fluid.

To assist in draining used fluid from chambers 270 and 272, while at the same time retaining contact lenses in chambers 270 and 272, cover member 260 can be rotated generally 90° so that strainers 274 and 276 would align over chambers 270 and 272. Thus, fluid can be either drained from, or rinsed into chambers 270 and 272 without any danger of contact lenses escaping. To then remove the contact lenses, cover member 260 would again be rotated 90° so that apertures 266 and 268 align with chambers 270 and 272.

FIG. 17 shows a lens holder 278 which functions similarly to lens holder 250 of FIG. 16. Instead of a separate threaded cover member containing strainers, a slot 280 extends across top wall 282 of lens holder 278. Strainer pieces 284 and 286 are slidable in grooves 288 along the sides of slot 280 between either a covering position (shown by strainer piece 284), or an open position (shown by strainer piece 286). Like the embodiment in FIG. 16, contact lenses can be easily inserted or removed from chambers 290 and 292, and strainer pieces 284 and 286 can be easily moved to hold them in chambers 290 and 292, even if fluid is dumped from the chambers, or fluid under pressure is rinsed into the chambers.

FIGS. 18 and 19 show a still further optional embodiment of the lens holder according to the invention. In this embodiment, lens holder base 294 has distributor head 296 extending up through top wall 298. Annular wall 300 extends above top wall 298 and surrounds distributor head 296 to form one large circular chamber 302. Annular wall has threads 304 on its outer vertical side.

A cover member 306, having interior threads (not shown) is threadably matable to threads 304 of annular wall 300. Cover member 306 includes cages 308 which extend downwardly from its bottom surface. It is to be understood that cages 308 basically form a basket wherein contact lenses can be inserted and supported, but that fluid can circulate into and around the interior of cages 308. Cover member 306 is further configured so that by turning dial 310, an underplate 312 turns. Rotatation of dial 310 90° would cause underplate 312 to rotate to the position shown in FIG. 19 which would cover openings 314, 316 to cages 308 and thus sealingly secure contact lenses within cages 308 and circular chamber 302. It is to be understood that other configurations for cover member 306 are possible to change it between openings to cages 308, and closing those openings.

It can be seen that in the embodiment of FIGS. 18 and 19, that circular chamber 302 can be filled with fluid, contact lenses can be inserted into cages 308, and then cover member 306 can be operated so that dial 310 is turned to close off openings 314 and 316 by under plate 312. Cover member 306 can then be threaded down onto lens holder 294. Alternatively, it is to be understood that under plate 312 might be operated by turning the perimeter of cover member 306. It is further to be understood that dial 310 might have openings to allow fluid from distributor head 296 to pass into cages 308 and 309, and cover member 306 might have a cap to cover it. Other embodiments and features are possible.

FIG. 20 shows a still further embodiment 318 according to the present invention. It operates on generally the same principles of the previous embodiments, except for the following. Lens holder 320 has an annular body 322 divided by a middle wall 324. A distributor head 326 having a stepped center bore 328 extends through the middle of middle wall 324.

FIG. 20 shows an exploded view of embodiment 318. An aerosol fluid container 330 having a depressible actuator tube 332 is insertable into the lower portion of stepped center bore 328 of distributor head 326. Stepped center bore 328 is configured so that if lens holder 320 is pushed downwardly, actuator tube 332 would also be pushed downwardly and expel fluid from aerosol fluid container 330 through and out the top of step center bore 328. When no pressure is put on lens holder 320, the biasing force of actuator tube 332 upwardly, would stop any expulsion of fluid from aerosol fluid container 330.

As further seen in FIG. 320, a cover cap 334 can be releaseably snapped into place over the top of lens holder 320. A dividing wall 336 would straddle distributor head 326, and divide circular chamber 338 into two chambers, one for each of the left and right contact lenses. Cover cap 334 has two hinged lids 340 and 342 which can be lifted to gain access to the two sides of circular chamber 338.

FIG. 20 also shows an optional feature and aspect of embodiment 318. An over cap 344 can be detachably positioned over cover cap 334. In the enclosed space in the interior of over cap 344, additional contact lens care products, chemicals, or items can be stored for easy and convenient access and use. For example, in embodiment 318, a baseboard 346 containing a plurality of dissolvable tablets 348 can be stored in over cap 344. As can be seen in FIG. 21, baseboard 346 can be circular and divided into various segments with indicia giving a user an indication as to when each tablet 348 should be used during a period of time. For example, numbers can be used for each day of the week to indicate when a certain tablet 348 should be inserted into circular chamber 338 which would then be filled with fluid which would dissolve a tablet so that it could achieve its lens care result.

FIG. 22 shows in cross-section cover cap 334 along lines 22—22 of FIG. 20. It can be seen that dividing wall 336 has slots 350 therein to allow fluid to disperse between both sides of dividing wall 336 and circular chamber 338.

FIG. 22 also shows in isolated cross-section distributor head 326. By comparing it to dividing wall 336 of cover cap 334, it can be seen that upper narrow portion 352 of distributor head 326 extends into wide bore portion 354 in dividing wall 336, but cannot pass into narrow bore portion 356 as it is wider than narrow bore portion 356. Therefore, fluid can pass through stepped center bore 328, distributor head 326 into narrow bore portion 356, and out into circular chamber 338 of lens holder 320.

FIG. 23 shows that in embodiment 318, the top of cover cap 334 would have a central rib 358. Arcuate raised portions 360 and 362 are placed at opposite ends of central rib 358. Hinged lids 340 and 342 would then hinge at their intersection with central rib 358, and have their sides defined by arcuate raised portions 360. Notches 364 and 366 on the underside of hinged lids 340 and 342 could be formed on their outer edge to allow grasping to open lids 340 and 342.

FIG. 24 shows a top plan view of lens holder 320. It can be seen that the top end 368 of distributor head 326 has two opposed notches 370 and 372 which would receive dividing wall 336 of cover cap 334, and hold it in non-rotatable position. Thus, it can be understood that embodiment 318 of FIGS. 20-24 would function as follows. Over cap 344 would be removed along with baseboard 346 holding tablets 348. Hinged lids 340 and 342 would be lifted sequentially and contact lenses would be inserted into the respective left and right sides defined by dividing wall 336 into circular chamber 338. If desired, an appropriate tablet 348 would be removed from baseboard 346 (which could be a blister pack or other well known tablet packaging means) and inserted into any part of circular chamber 338 through hinged lids 340 or 342.

Hinged lids 340 and 342 would then be secured down, and lens holder 320 would be pressed downwardly against aerosol fluid container 330. Fluid would then be conducted from aerosl fluid container 330 through distributor head 326 into circular chamber 338. Slots 350 would allow equal distribution of the fluid, and the fluid would act upon any tablet 348 to dissolve the same. Movement of the fluid would also carry the dissolved tablet 348 to all parts of circular chamber 338. Baseboard 346 and overcap 344 could then be repositioned over cover cap 334 and embodiment 318 could be left for the tablet and fluid to operate on the contact lenses. After an appropriate time, or as desired, overcap 344 and baseboard 346 would again be removed, and contact lenses could be removed and the fluid dumped. Lens holder 320 could then be rinsed and cleaned and be prepared for another use.

It is further to be understood that lens holder 320 of embodiment 318 could also be used separately as a lens holder with or without overcap 344.

FIG. 25 shows embodiment 374, which is similar to embodiment 318 of FIG. 20 except for the following. Lens holder 376 has a lower wall 378 through which extends distributor head 380. An upper wall 382 has hinged lids 384 and 386. Furthermore, divider wall 388 (particularly FIG. 28, functions like that of embodiment 318 as shown in FIGS. 20 and 22), having slits therein to allow transfer of fluid between opposite sides of lens holder 376. A baseboard holding tablets such as shown in FIG. 21 could then be stored in the space between upper wall 382 and screw cap 392 on lens holder . 376.

FIG. 26 shows that upper wall 382 is of a configuration similar to cover cap 334 of FIG. 24, and shows the hinged lids, and schematically shows by arrows how liquid can be dispersed on opposite sides of divider wall 388.

Finally, FIG. 27 shows in isolated detail divider wall 388, and the operation of hinged lids 384, 386 and slits 390.

It will be appreciated that the present invention can take many forms and embodiments. The true essence and spirit of this invention are defined in the appended claims, and it is not intended that the embodiments of the invention presented herein should limit the scope thereof. It can therefore be seen that the invention achieves at least all of its stated objectives.

What is claimed is:

1. A means for both storing and caring for contact lenses comprising:

first container means for containing and supporting a contact lens, and for receiving and containing, as desired, a fluid used in contact lens care, the first container means including an enclosable fluid-tight chamber and a cap means, moveable between open and closed positions to enclose the first container means and allow insertion and removal of the contact lens;

connection means for removably securing the first container means to the second container means; and conduit means extending between and providing fluid communication between the first and second container means.

2. The means of claim 1 wherein the first container means comprises an enclosed fluid tight chamber having an access opening for insertion and removal of the contact lens.

3. The means of claim 1 wherein the first container contains and supports a pair of contact lenses.

4. The means of claim 3 wherein the first container includes means to separate each contact lens.

5. The means of claim 3 wherein the first container comprises first and second separate chambers.

6. The means of claim 1 wherein the first container is positioned in an assembly which includes at least part of the conduit means.

7. The means of claim 1 wherein the second container is separable from the conduit means.

8. The means of claim 1 wherein the second container is separable from the first container means.

9. The means of claim 1 wherein the conduit means comprises an enclosed fluid pathway between the first and second container means.

10. The means of claim 1 wherein the cap means blocks the conduit means between the first and second containers when in a closed position.

11. The means of claim 1 wherein the conduit means includes a valve means.

12. A system for storing and caring of contact lenses comprising:

a contact lens holder means for removably supporting and containing fluids and at least one contact lens;

a fluid conduit means positioned in the contact lens holder means for conducting fluid to the contact lens holder means and;

an interchangeable fluid container means removably attachable to the fluid conduit means and contact lens holder means for putting the contact lens holder means into selective fluid communication with a fluid used in the care of contact lenses.

13. A means for storing and caring for contact lenses comprising:

a base member including one or more chambers defined by fluid-tight walls into which can be placed a contact lens and fluid used in the care of contact lenses, a cap securable to the base member which can adjustably cover at least a portion of each chamber to prevent loss of a contact lens from the chamber during storage or caring for the contact lens, a tubular duct in the base member having a first open end and a second open end, a distributor member connected to the first open end of the duct for distributing fluid passing through the duct to each chamber; and connection means on the base for interchangeable attachment of a fluid container to the base member so that the second end of the duct is in fluid communication with any fluid in the fluid container.

* * * * *